(12) United States Patent
Tanaka et al.

(10) Patent No.: US 8,330,458 B2
(45) Date of Patent: Dec. 11, 2012

(54) NONDESTRUCTIVE INSPECTION APPARATUS USING SQUID MAGNETIC SENSOR

(75) Inventors: Saburo Tanaka, Toyohashi (JP); Yoshimi Hatsukade, Toyohashi (JP)

(73) Assignee: National University Corporation TOYOHASHI UNIVERSITY OF TECHNOLOGY, Toyohashi-shi, Aichi (JP)

( * ) Notice: Subject to any disclaimer, the term of this patent is extended or adjusted under 35 U.S.C. 154(b) by 308 days.

(21) Appl. No.: 12/919,227

(22) PCT Filed: Mar. 5, 2009

(86) PCT No.: PCT/JP2009/054125
§ 371 (c)(1), (2), (4) Date: Aug. 25, 2010

(87) PCT Pub. No.: WO2009/110529
PCT Pub. Date: Sep. 11, 2009

(65) Prior Publication Data
US 2011/0031967 A1    Feb. 10, 2011

(30) Foreign Application Priority Data
Mar. 5, 2008   (JP) ................. 2008-054360

(51) Int. Cl.
*G01R 33/12* (2006.01)
*G01N 27/72* (2006.01)

(52) U.S. Cl. ......... 324/248; 324/228; 324/244; 324/262

(58) Field of Classification Search .................. 324/248, 324/228, 244, 262
See application file for complete search history.

(56) References Cited

U.S. PATENT DOCUMENTS
6,218,830 B1   4/2001   Yoshida et al.

FOREIGN PATENT DOCUMENTS

| | | |
|---|---|---|
| JP | 5-255768 | 10/1993 |
| JP | 07-077516 | 3/1995 |
| JP | 10-038854 | 2/1998 |
| JP | 10-194425 | 7/1998 |
| JP | 2005-183142 | 7/2005 |
| JP | 2005-351804 | 12/2005 |

OTHER PUBLICATIONS
International Search Report in PCT/JP2009/054125, dated Apr. 7, 2009.

*Primary Examiner* — Reena Aurora
(74) *Attorney, Agent, or Firm* — Bacon & Thomas, PLLC

(57) ABSTRACT

There is provided a nondestructive inspection apparatus using a SQUID magnetic sensor which allows nondestructive and accurate detection of magnetic particles in an insulator such as an electronic device or in a magnetizable member. The nondestructive inspection apparatus using the SQUID magnetic sensor comprises: a magnet for horizontal magnetization 4, the magnet applying a magnetic field to a specimen in the longitudinal direction of the specimen 3'; an inspection unit on which a specimen 3 is set, the specimen 3 being horizontally magnetized in the longitudinal direction by the magnet for horizontal magnetization 4; and belt conveyers 2, 5 for conveying the horizontally magnetized specimen 3; and a gradiometer 8 for detecting a particle horizontally magnetized along with a magnetizable member as the horizontally magnetized specimen 3.

14 Claims, 13 Drawing Sheets

(a)

(b)

(c)

(a)

(b)

(c)

(a)

(b)

(a)

(b)

(a)

(b)

(a)

(b)

NONDESTRUCTIVE INSPECTION APPARATUS USING SQUID MAGNETIC SENSOR

BACKGROUND OF THE INVENTION

1. Field of the Invention

The present invention relates to a nondestructive inspection apparatus using a SQUID magnetic sensor for conducting nondestructive inspection of specimens.

2. Description of the Related Art

In the field of nondestructive inspection of structures formed of such as metal materials or conductive composite materials, the eddy current testing which detects cracks by inducing eddy current, the ultrasonic testing using ultrasonic waves, and the X-ray testing using X-rays have been put into practical use. Furthermore, a nondestructive inspection method using a SQUID (Superconducting Quantum Interference Device) magnetic sensor has been proposed (see Patent Document 1 below).

Patent Document 1: JP 07-077516 A
Patent Document 2: Japanese Patent No. 3152074

SUMMARY OF THE INVENTION

The conventional eddy current testing mentioned above requires induction of high-frequency eddy current in order to achieve a high sensitivity, so that there is a problem that the inspection cannot be conducted other than in the range of a few tenth millimeters in the vicinity of a sample surface. Moreover, the sensitivity thereof is insufficient in comparison with a SQUID magnetic sensor or the like. In addition, although the conventional ultrasonic testing is an excellent inspection method for uniform metal materials, the precise testing cannot be conducted for composite materials which have an internal complex structure because such materials reflect or scatter the ultrasonic wave at the interface. Although the conventional X-ray testing is also an excellent inspection method, it is less versatile because X-rays are generally cumbersome and particular facilities and qualifications are required in view of exposure to the X-rays.

On the other hand, since the nondestructive inspection method using the SQUID magnetic sensor uses the SQUID magnetic sensor which have a very high sensitivity even in the low-frequency range, it allows detection of much deeper portions and much microscopic defects as compared to the eddy current testing. In addition, it has been proven that the method is less likely to be affected by the internal complex structure than the ultrasonic testing and is applicable to the composite materials. Moreover, it is less dangerous as compared to the X-ray testing, and particular facilities and qualifications are not required. Furthermore, a nondestructive inspection apparatus has been proposed wherein a magnetic field generation means is provided for perpendicularly magnetizing an elongated specimen such as a linear body just prior to the inspection (see Patent Document 2 above). However, the apparatus uniformly magnetizes the elongated specimen such as a linear body, which is not suitable for detecting a magnetized member mixed in an electronic device or the like.

Although there is a strong need particularly to detect magnetic particles in an insulator such as an electronic device or in a magnetizable member nondestructively and accurately, such nondestructive inspection apparatuses have not yet been proposed. In view of the above-described situation, the present invention is intended to provide a nondestructive inspection apparatus using a SQUID magnetic sensor that can detect magnetic particles in an insulator such as an electronic device or in a magnetizable member nondestructively and accurately.

In order to achieve the object described above, the present invention provides the following:

[1] A nondestructive inspection apparatus using a SQUID magnetic sensor comprising: a magnet for horizontal magnetization, the magnet applying a magnetic field to a specimen in the longitudinal direction of the specimen; an inspection unit on which the specimen is set, the specimen being horizontally magnetized in the longitudinal direction by the magnet for horizontal magnetization; a belt conveyer for conveying the horizontally magnetized specimen; and a gradiometer for detecting a particle horizontally magnetized along with a magnetizable member as the horizontally magnetized specimen.

[2] The nondestructive inspection apparatus using the SQUID magnetic sensor according to [1], wherein the belt conveyer includes a first belt conveyer serving as a magnetizing stage on which the magnetic field is applied to the specimen, and a second belt conveyer disposed separately from the first belt conveyer and serving as an inspection stage on which the specimen is inspected.

[3] The nondestructive inspection apparatus using the SQUID magnetic sensor according to [1], further comprising a cleaning means for removing a foreign material adhering to the belt conveyer after applying the magnetic field.

[4] The nondestructive inspection apparatus using the SQUID magnetic sensor according to [1], wherein the magnetizable member is disposed in a non-magnetized member.

[5] The nondestructive inspection apparatus using the SQUID magnetic sensor according to [4], wherein the non-magnetized member is an insulating member.

[6] The nondestructive inspection apparatus using the SQUID magnetic sensor according to [5], wherein the insulating member is ceramics.

[7] The nondestructive inspection apparatus using the SQUID magnetic sensor according to [1], wherein the magnetizable member is a conductive foil having an active material applied thereto.

[8] The nondestructive inspection apparatus using the SQUID magnetic sensor according to [7], wherein the conductive foil is a copper foil or an aluminum foil.

[9] The nondestructive inspection apparatus using the SQUID magnetic sensor according to [1], wherein the particle is placed on or in the magnetizable member.

[10] The nondestructive inspection apparatus using the SQUID magnetic sensor according to [4], wherein the particle is placed in the non-magnetized member.

[11] The nondestructive inspection apparatus using the SQUID magnetic sensor according to [1], wherein the particle is a magnetic material.

[12] The nondestructive inspection apparatus using the SQUID magnetic sensor according to [11], wherein the magnetic material is iron, nickel, cobalt, or an alloy containing any of iron, nickel, and cobalt.

[13] The nondestructive inspection apparatus using the SQUID magnetic sensor according to [1], wherein the magnet for horizontal magnetization is a permanent magnet.

[14] The nondestructive inspection apparatus using the SQUID magnetic sensor according to [1], wherein one-dimensional scanning is conducted by moving the horizontally magnetized specimen in the X direction while the gradiometer remains stationary.

[15] The nondestructive inspection apparatus using the SQUID magnetic sensor according to [1], wherein the specimen is also inspected in the lateral direction simultaneously by disposing a plurality of gradiometers in the direction perpendicular to the moving direction of the specimen.

DESCRIPTION OF THE PREFERRED EMBODIMENTS

A nondestructive inspection apparatus using the SQUID magnetic sensor comprises: a magnet for horizontal magnetization for applying a magnetic field in the longitudinal direction of a specimen; an inspection unit on which the specimen is set, the specimen being horizontally magnetized in the longitudinal direction by the magnet for horizontal magnetization; and a belt conveyer for conveying the horizontally magnetized specimen; and a gradiometer for detecting a particle horizontally magnetized along with a magnetizable member as the horizontally magnetized specimen.

According to the present invention, the following effects can be achieved.

(1) Particles mixed in a specimen and their positional information can be detected nondestructively and accurately.

(2) Since it is configured so that a magnetic field is applied to the specimen on a first conveyer and inspection of the specimen is conducted on a second conveyer disposed separately from the first conveyer, a magnetic noise on an inspection stage is removed and the accurate inspection can be conducted.

(3) Even if the horizontally magnetized specimen contains a ferromagnetic material, such as iron, which is strongly magnetized, a magnetic field generated by passing the specimen through the high-temperature superconductive SQUID magnetic sensor is only generated at the both ends of the ferromagnetic material and in a magnetized foreign material (particles), allowing the nondestructive inspection to be conducted which can detect the magnetized foreign material (particles) with high accuracy. In this case, the detection of the foreign material (particles) becomes difficult if it is present in the vicinity of the both ends of the magnetic material. However, a signal from the foreign material can be detected by preliminarily storing a signal pattern of the specimen without the foreign material (particles) and subtracting the signal pattern from the signal from the specimen containing the foreign material (particles).

EMBODIMENTS

Hereinbelow, embodiments of the present invention will be described in detail.

Figure 1:
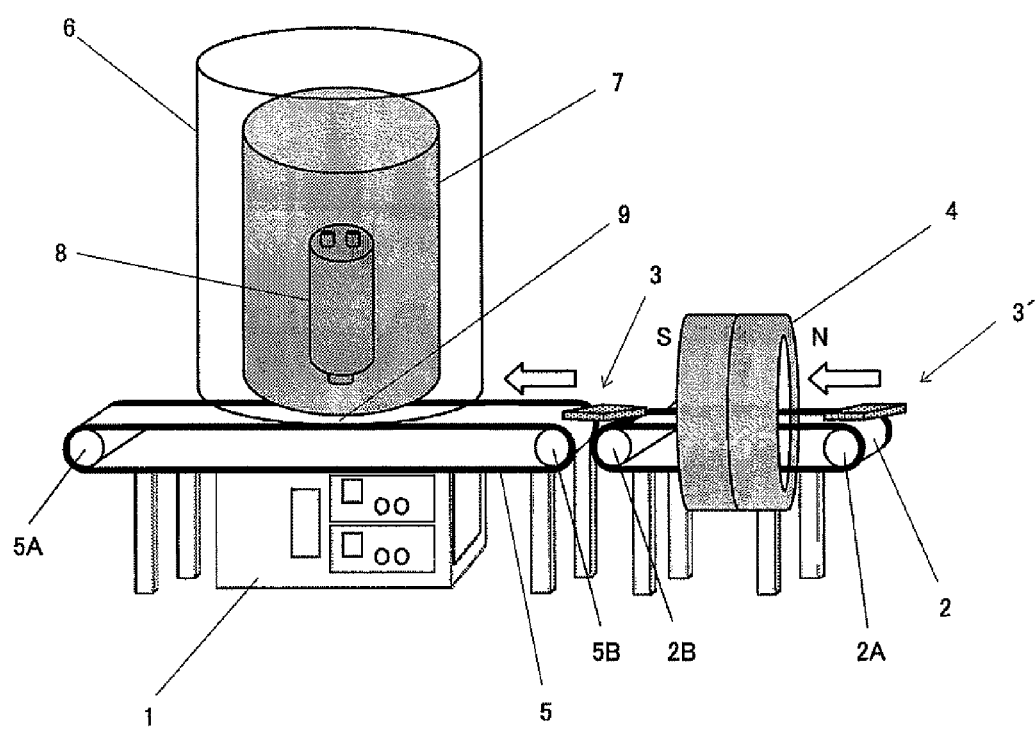
FIG. 1 is a diagrammatic view of a nondestructive inspection apparatus using a SQUID magnetic sensor, illustrating an embodiment of the present invention.

FIG. 1 is a diagrammatic view of a nondestructive inspection apparatus using a SQUID magnetic sensor, illustrating an embodiment of the present invention.

In this figure, reference numeral 1 denotes a control unit, 2 denotes a first conveyer (polarizing stage), 2A denotes a motorized driving pulley on a driving side of the first conveyer 2, 2B denotes a driven pulley of the first conveyer 2, 3' denotes an unpolarized specimen, 4 denotes a magnet for horizontal magnetization (tunnel-shaped permanent magnet) used to magnetize the unpolarized specimen 3' in the longitudinal direction, 5 denotes a second conveyer (inspection stage) disposed separately from the first conveyer (polarizing stage) 2, 5A denotes a motorized driving pulley on a driving side of the second conveyer 5, and 5B denotes a driven pulley of the second conveyer 5. A polarized specimen 3 is conveyed by the second conveyer 5 disposed separately from the first conveyer (polarizing stage) 2, and inspected on the second conveyer 5. Reference numeral 6 denotes a magnetic shield, 7 denotes a SQUID cooling container, 8 denotes a SQUID sensor (gradiometer), and 9 denotes an inspection unit on which the magnetized specimen 3 is inspected. In order to avoid the influence by electromagnetic waves, the magnetic shield 6 may include an electromagnetic shield configured by a conductive material such as aluminum.

In this manner, the unpolarized specimens 3 are conveyed by the first conveyer 2 through the tunnel-shaped magnet for horizontal magnetization 4, i.e., the permanent magnet with its S and N poles being disposed in the longitudinal direction, so as to be magnetized sequentially. The polarized specimens 3 are conveyed by the second conveyer 5 to the inspection unit 9 of the SQUID magnetic sensor 8. Here, the tunnel-shaped magnet for horizontal magnetization 4 may be configured by electromagnets. In addition, the specimens 3 may be polarized sequentially without stopping the conveyer 2 by configuring a semicircular permanent magnet or electromagnet having an S pole on the one end and an N pole on the other end and passing the specimen 3 therethrough.

In this manner, it is desirable to configure the first conveyer (polarizing stage) 2 and the second conveyer (inspection stage) 5 separately. Such a configuration can minimize the influence of polarization to the conveyers themselves due to adhesion of the foreign material to the conveyers, so that a magnetic noise is removed and the accurate inspection can be conducted.

Here, although the first and second conveyers described above employ endless belt conveyers driven by a motor which is not illustrated in the figure, horizontal type conveyers as used in conveyer-belt sushi bars or electrostatically driven belt conveyers may be used instead.

In addition, in the case where a single belt conveyer is employed instead of separate first and second conveyers, it is desirable to give particular consideration to inhibit the generation of a magnetic noise at the measurement due to adhesion of the foreign material by disposing the magnet for horizontal magnetization and the gradiometer in a clean booth to prevent adhesion of the foreign material to the conveyer and polarization thereof or disposing a cleaning means such as an adhesive roller between the magnet for horizontal magnetization and the gradiometer to remove the foreign material adhering to the conveyer.

Figure 2:
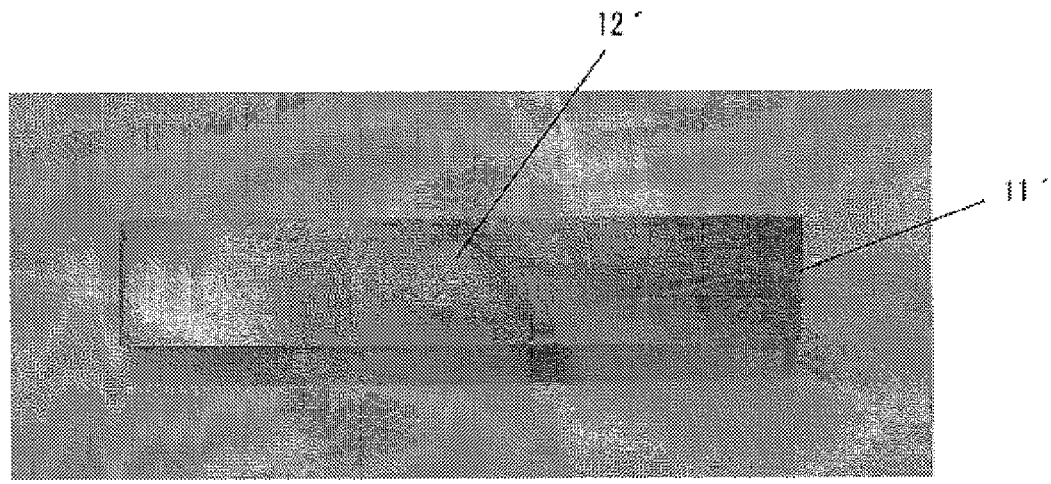
FIG. 2 is a diagram showing a specimen to be provided for one-dimensional scan evaluation by the nondestructive inspection apparatus using the SQUID magnetic sensor, illustrating a first embodiment of the present invention.
Figure 2:
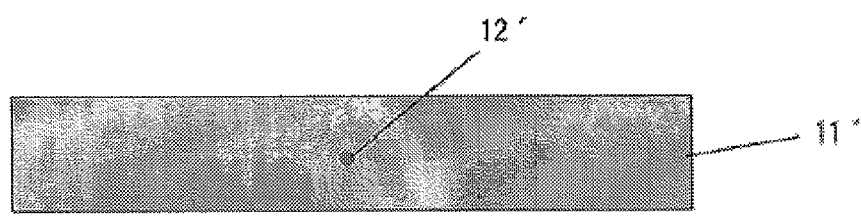
Figure 2:
Figure 3:
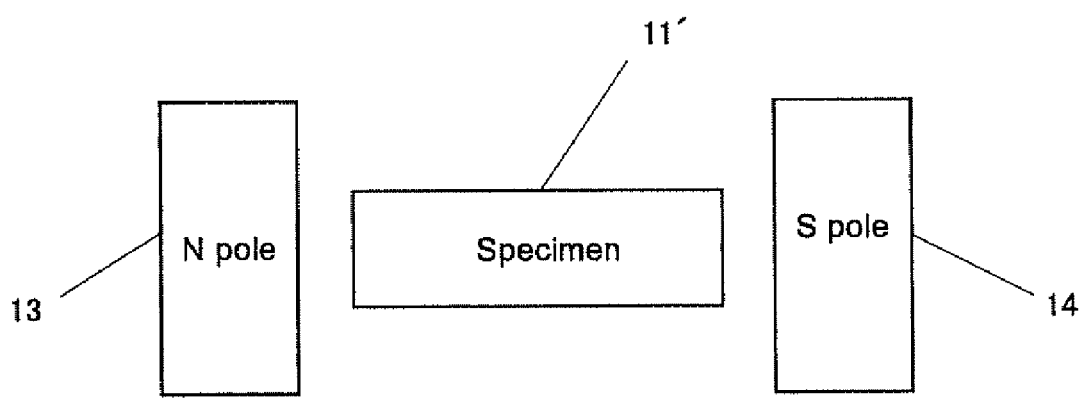
FIG. 3 is a diagram showing a polarized state of the specimen in the first embodiment of the present invention.
Figure 4:
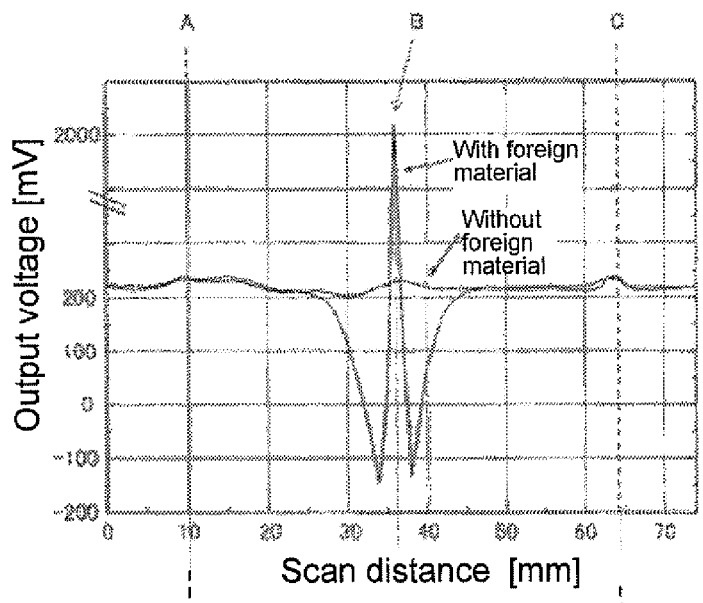
FIG. 4 is a diagram showing one-dimensional scanning of the specimen in the first embodiment of the present invention.
Figure 4:
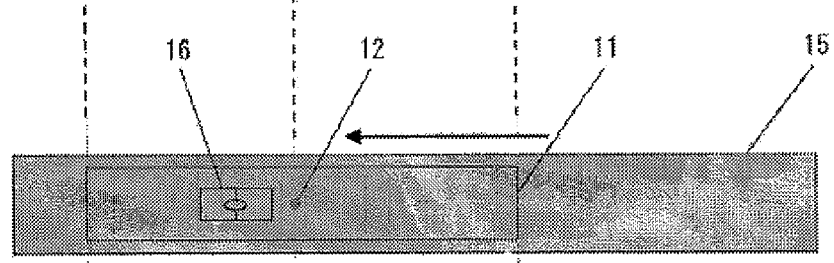
Figure 4:
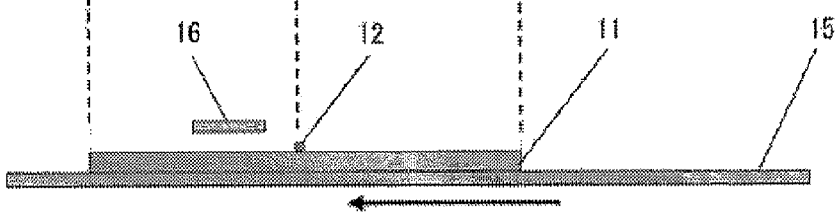

FIG. 2 is a diagram showing the specimen to be provided for one-dimensional scan evaluation by the nondestructive inspection apparatus using the SQUID magnetic sensor, illustrating a first embodiment of the present invention, wherein FIG. 2(a) is a substitute photograph showing the specimen, FIG. 2(b) is a top view of the specimen, and FIG. 2(c) is a front view; FIG. 3 is a diagram showing a polarized state of the specimen; and FIG. 4 is a diagram showing one-dimensional scanning of the specimen, wherein FIG. 4(a) is a diagram showing a result of the one-dimensional scanning of the specimen, FIG. 4(b) is a top view showing a state of the one-dimensional scanning, and FIG. 4(c) is a front view thereof.

In this first embodiment, as shown in FIG. 2, a stainless particle (SUS304, sphere with 0.3 mm in diameter) 12' is placed on a brass plate 11' (10 mm in width, 54 mm in length) as a magnetizable strip member. As shown in FIG. 3, the unpolarized brass plate 11' having the stainless particle 12' is magnetized using two permanent magnets 13, 14 having a surface magnetic flux density of 0.15 T. Then, as shown in FIGS. 4(b) and (c), a brass plate 11 having a polarized stainless particle 12 is conveyed on a second conveyer 15 and scanned one dimensionally by a gradiometer 16 in a fixed position. The scanning result is as shown in FIG. 4(a), wherein A and C sections of FIG. 4(a) correspond to the scanning results of the ends of the polarized brass plate 11, and a B section of FIG. 4(a) corresponds to the scanning result of the polarized stainless particle 12. That is, it can be detected here that the stainless particle 12 is present at a position of 26 mm from the A section, or the one end of the brass plate 11, in the longitudinal direction of the brass plate 11 and of 28 mm from the C section, or the other end of the brass plate 11, in the longitudinal direction of the brass plate 11. In other words, it should be noted that the brass plate 11 has a function as a scale for measuring the position of the stainless particle 12.

For the sake of comparison, the figure also shows the one-dimensional scanning result of the specimen with no stainless particle being present. In this manner, in the one-dimensional scanning by the nondestructive inspection apparatus using the SQUID magnetic sensor of the first embodiment of the present invention, a significant gradient magnetic field appears and the presence of the stainless particle 12 including its positional information is accurately measured.

Here, although the detection of the foreign material (particles) becomes difficult if it is present in the vicinity of the both ends of the magnetic material, a signal from the foreign material can be detected by preliminarily storing a signal pattern of the specimen without the foreign material (particles) and subtracting the signal pattern from the signal from the specimen containing the foreign material (particles).

Figure 5:
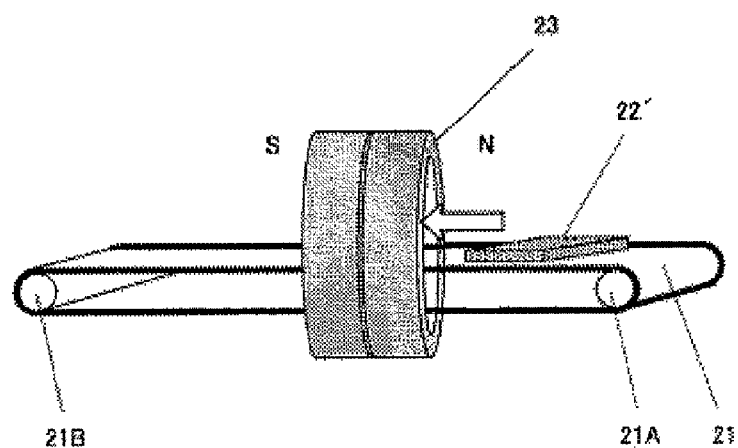
FIG. 5 is a diagram showing the specimen to be provided for the one-dimensional scan evaluation by the nondestructive inspection apparatus using the SQUID magnetic sensor and a result of the one-dimensional scan evaluation, illustrating a second embodiment of the present invention.
Figure 5:
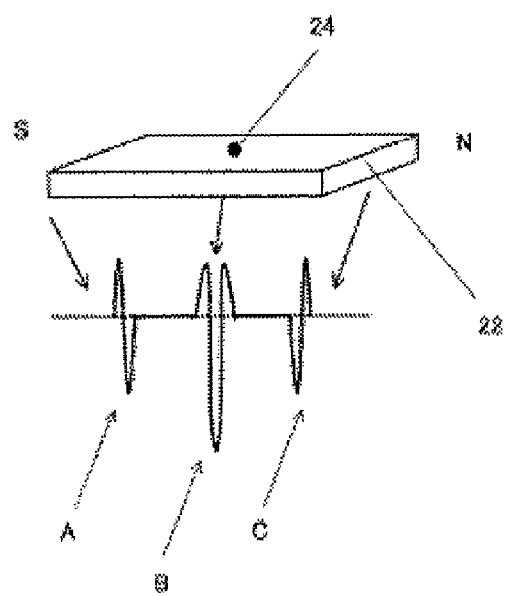
Figure 6:
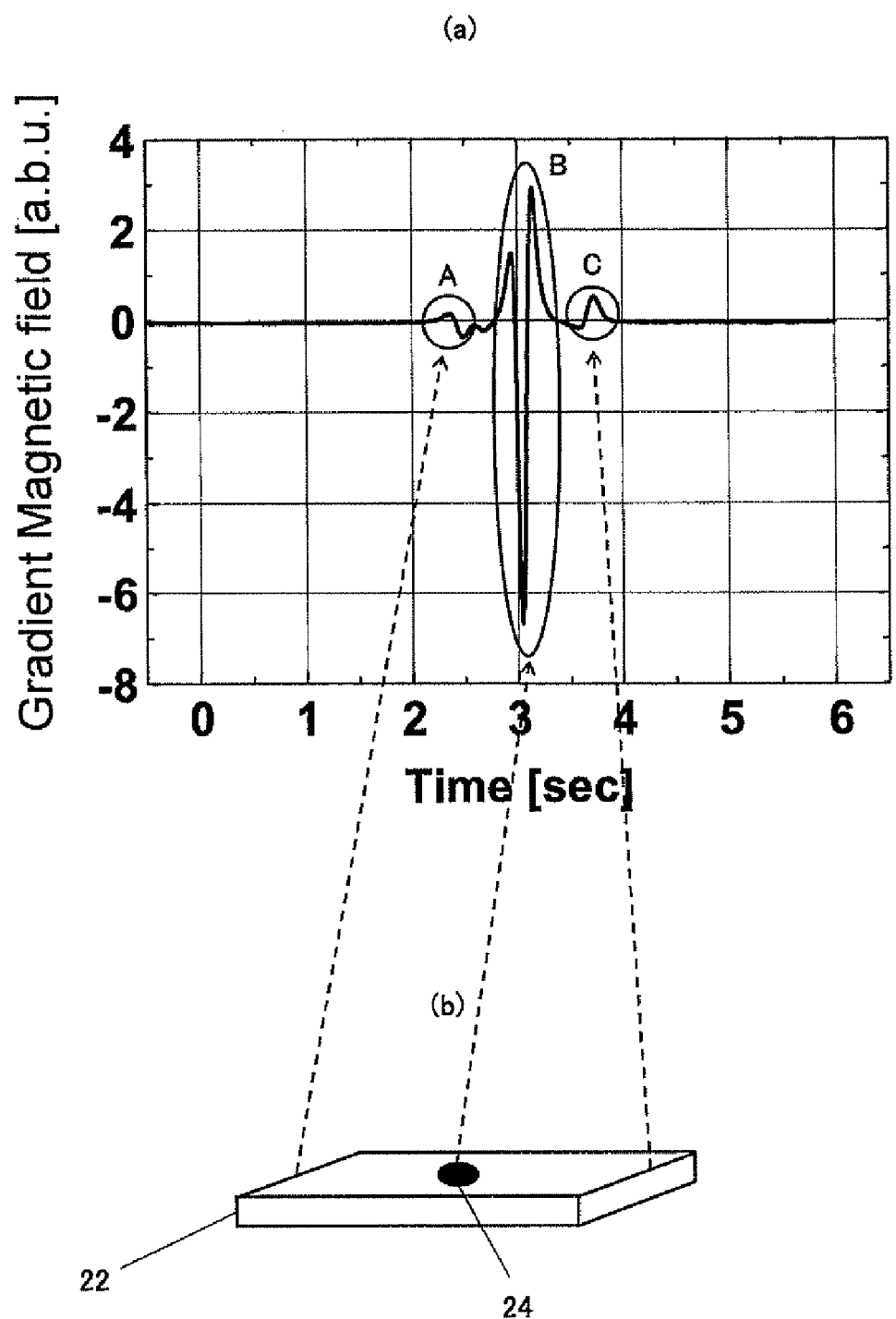
FIG. 6 is a diagram showing a specific example of the second embodiment of the present invention.

FIG. 5 is a diagram showing the specimen to be provided for the one-dimensional scan evaluation by the nondestructive inspection apparatus using the SQUID magnetic sensor and a result of the one-dimensional scan evaluation, illustrating a second embodiment of the present invention, wherein FIG. 5(a) is a diagram showing a state of polarization of the specimen and FIG. 5(b) is a diagram showing the specimen and an inspection result thereof; and FIG. 6 is a diagram showing a specific example thereof, wherein FIG. 6(a) is a diagram showing a result of an actual measurement and FIG. 6(b) is a diagram showing the polarized specimen which is the brass plate having tungsten carbide (90 μm in diameter) adhering thereto as the particle.

As shown in FIG. 5(a), an unpolarized specimen 22' is conveyed by a first belt conveyer 21 and polarized by passing it through a tunnel-shaped magnet for horizontal magnetization 23. As shown in FIG. 5(b), in the case where a specimen 22 is configured by the polarized brass plate and tungsten carbide (90 μm in diameter) 24 as the particle adhering thereto, a gradient magnetic field is detected at the position of the both ends of the specimen 22 and tungsten carbide 24 as the particle.

Specifically, with the inspection condition of standoff: 3.6 mm, velocity: 2.7 m/min., and magnetic field: 0.2 T, in the polarized specimen 22 having tungsten carbide (90 μm in diameter) 24 adhering thereto as shown in FIG. 6(b), the gradient magnetic field as seen in an A section of FIG. 6(a) was observed at the S pole of the front end of the specimen 22, the gradient magnetic field as seen in a B section of FIG. 6(a) was observed at the position of the tungsten carbide (90 μm in diameter) 24 as the particle of the specimen 22, and the gradient magnetic field as seen in a C section of FIG. 6(a) was measured at the N pole of the rear end of the specimen 22. In this manner, the gradient magnetic field similar to that of FIG. 5 (b) was shown by the measurement using the gradiometer.

Figure 7:
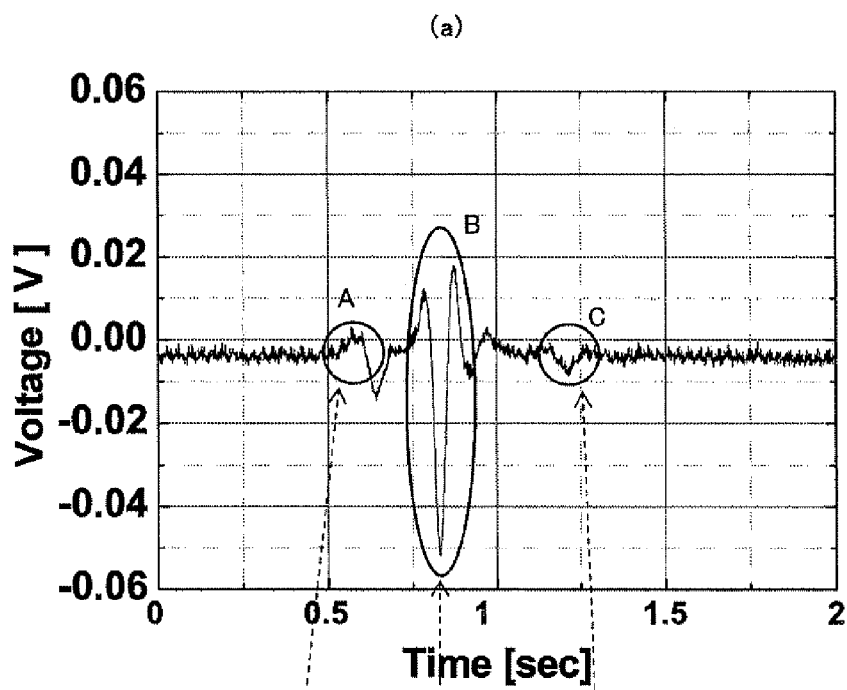
FIG. 7 is a diagram showing the specimen to be provided for the one-dimensional scan evaluation by the nondestructive inspection apparatus using the SQUID magnetic sensor and a result of the one-dimensional scan evaluation, illustrating a third embodiment of the present invention.
Figure 7:
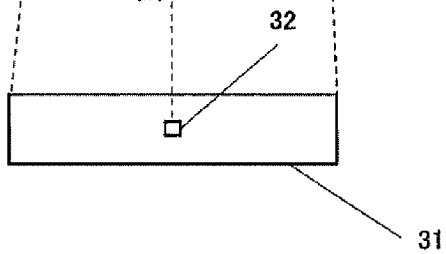

FIG. 7 is a diagram showing the specimen to be provided for the one-dimensional scan evaluation by the nondestructive inspection apparatus using the SQUID magnetic sensor and a result of the one-dimensional scan evaluation, illustrating a third embodiment of the present invention, wherein FIG. 7(a) is a diagram showing a measurement result and FIG. 7(b)

is a diagram showing the polarized specimen formed of the brass plate having nickel (50 μm □) as the particle adhering thereto.

Specifically, with the inspection condition of magnetization direction: horizontal magnetization, approximately 0.2 T, standoff: 3.3 mm, velocity: 6 m/min., and conversion factor for magnetic flux: 3.4 nT/V, in the inspection of the polarized specimen formed of a brass plate 31 having nickel (50 μm □) 32 adhering thereto by the SQUID magnetic sensor (gradiometer), the gradient magnetic field was observed as shown in FIG. 7(a). That is, the gradient magnetic field of the A, B, and C sections correspond to that of the leading end of the brass plate 31, that of nickel 32, and that of the trailing end of the brass plate 31, respectively.

Figure 8:
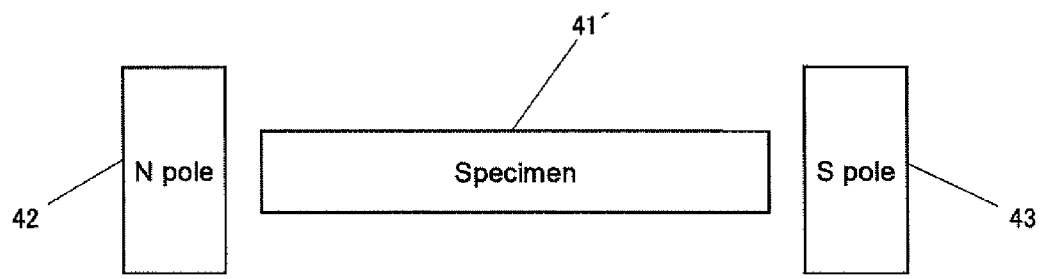
FIG. 8 is a diagram showing a polarized state of the specimen to be provided for two-dimensional scan evaluation by the nondestructive inspection apparatus using the SQUID magnetic sensor, illustrating a fourth embodiment of the present invention.
Figure 9:
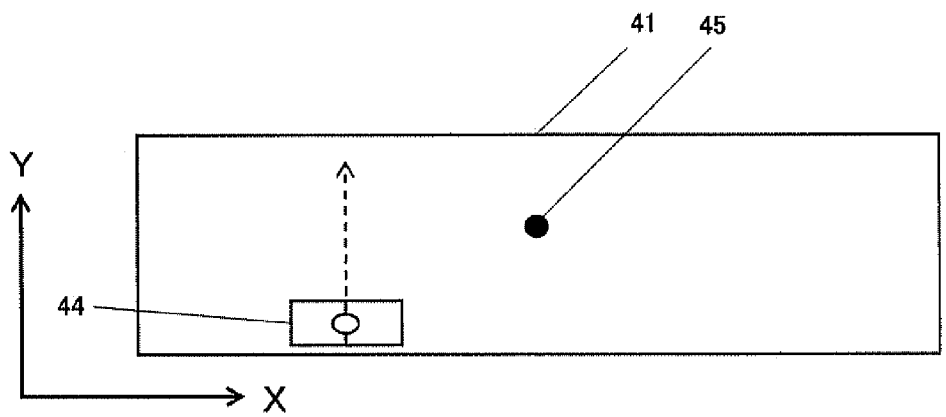
FIG. 9 is a diagrammatic view of the nondestructive inspection apparatus using the SQUID magnetic sensor (gradiometer) for conducting two-dimensional scanning (scanning in the X-axis and Y-axis directions) of the specimen, illustrating the fourth embodiment of the present invention.
Figure 10:
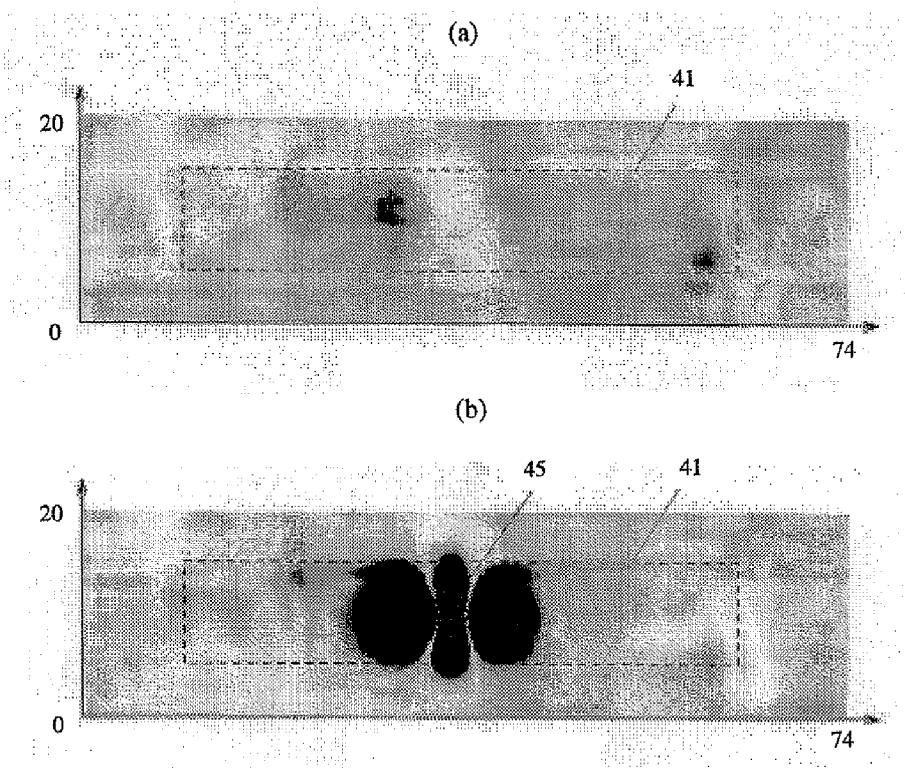
FIG. 10 is a diagram showing a scanning result of the specimen, illustrating the fourth embodiment of the present invention.

FIG. 8 is a diagram showing a polarized state of the specimen to be provided for two-dimensional scan evaluation by the nondestructive inspection apparatus using the SQUID magnetic sensor, illustrating a fourth embodiment of the present invention; FIG. 9 is a diagrammatic view of the nondestructive inspection apparatus using the SQUID magnetic sensor (gradiometer) for conducting two-dimensional scanning (scanning in the X-axis and Y-axis directions) of the specimen; and FIG. 10 is a diagram showing a scanning result of the specimen, wherein FIG. 10(a) is a diagram showing a result in the case where the particle is not present on the specimen and FIG. 10(b) is a diagram showing a result in the case where the particle is present on the specimen.

In this embodiment, as shown in FIG. 8, an unpolarized specimen 41' is polarized using two permanent magnets 42, 43 having a surface magnetic flux density of 0.15 T. As shown in FIG. 9, by scanning a gradiometer 44 also relatively in the direction (Y-axis direction) perpendicular to the moving direction of a polarized specimen 41, a magnetized particle 45 adhering to the polarized specimen 41 can be inspected simultaneously in the longitudinal direction (X-axis direction) and the lateral direction (Y-axis direction).

In this manner, while the scanning result of the specimen 41 having no magnetic particle thereon does not show any particular gradient magnetic field as shown in FIG. 10(a), if a particle (SUS304) 45 is present, a strong gradient magnetic field is observed at its position, as shown in FIG. 10(b), so that the presence of the particle 45 on the specimen 41 is measured.

Here, the embodiment described above is configured to conduct the scanning in the direction perpendicular to the moving direction of the polarized specimen 41, so that the presence of the particle can be accurately inspected regardless of the location thereof on the specimen 41.

Figure 11:
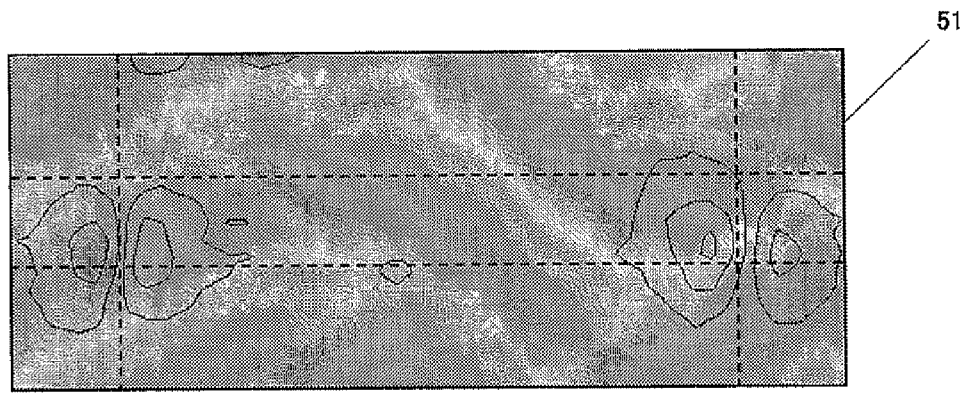
FIG. 11 is a diagram showing an inspection result by the gradiometer of a ceramic electronic device (specimen) with magnetic particle not being present to be provided for the two-dimensional scan evaluation by the nondestructive inspection apparatus using the SQUID magnetic sensor, illustrating a fifth embodiment of the present invention.
Figure 12:
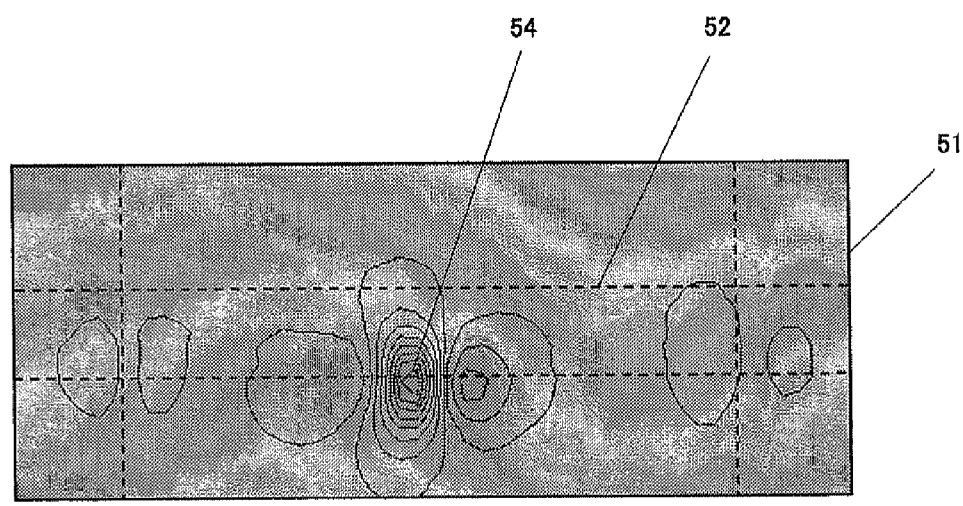
FIG. 12 is a diagram showing an inspection result by the gradiometer of the ceramic electronic device (specimen) with the magnetic particle being present, illustrating the fifth embodiment of the present invention.

FIG. 11 is a diagram showing an inspection result by the gradiometer of a ceramic electronic device (specimen) with the magnetic particle not being present to be provided for the two-dimensional scan evaluation by the nondestructive inspection apparatus using the SQUID magnetic sensor, illustrating a fifth embodiment of the present invention; FIG. 12 is a diagram showing an inspection result by the gradiometer of the ceramic electronic device (specimen) with the magnetic particle being present; and FIG. 13 is a diagram showing the specimen with the particle being present within ceramic, wherein FIG. 13(a) shows a top view of the specimen and FIG. 13(b) shows a side view of the specimen.

Figure 13:
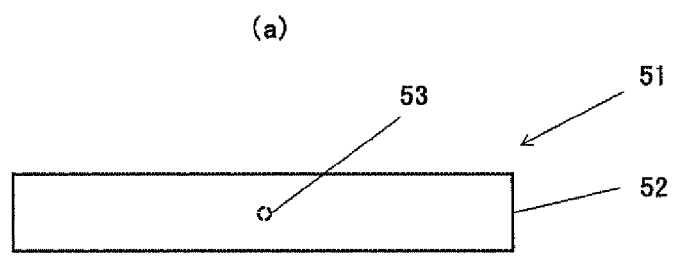
FIG. 13 is a diagram showing the specimen with the particle being present within ceramic, illustrating the fifth embodiment of the present invention.
Figure 13:
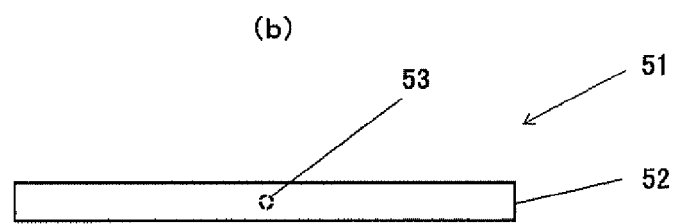

In FIG. 13, reference numeral 51 denotes an electronic device (specimen) sealed in ceramic as an insulator member, 52 denotes a magnetizable member provided in the electronic device (specimen) 51, and 53 denotes Co (0.1 mm in diameter) as the particle present in the magnetizable member 52. While, in a typical example of the ceramic electronic device (specimen) 51, the magnetizable member includes a ceramic member impurified with a magnetizable substance (i.e., a ceramic member as an insulator which is made to be magnetizable by incorporating the magnetizable substance), it is not limited thereto.

In this manner, even if the particle 53 is present in the ceramic electronic device as the insulator or in the ceramic member which is made to be magnetizable, a significant gradient magnetic field 54 is observed by the measurement using the gradiometer at the position of the particle 53, as shown in FIG. 12, so that the presence of the particle is measured.

Figure 14:
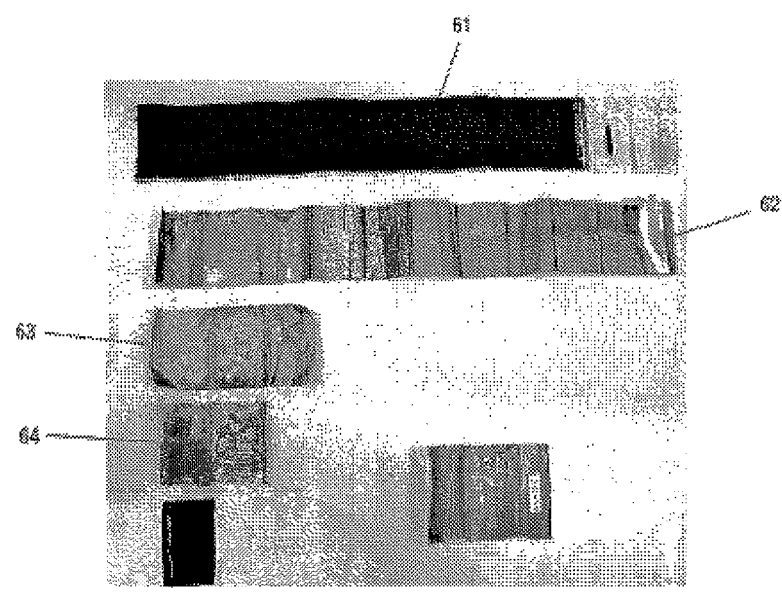
FIG. 14 is a diagram showing a lithium battery electrode plate to be measured by the nondestructive inspection apparatus using the SQUID magnetic sensor of the present invention.

FIG. 14 is a diagram showing a lithium battery electrode plate to be measured by the nondestructive inspection apparatus using the SQUID magnetic sensor of the present invention.

Also in the case where the particle is present on a copper foil coated with an active material (positive pole) 61 used as a lithium battery electrode plate, an Al foil (positive pole) 62, a Cu foil (negative pole) 63, a separator (resin sheet) 64 or the like as shown in FIG. 14, the presence of the particle can be measured by the measurement method described above. In particular, as long as the member, even if it is an insulator, is impurified with the magnetizable substance such as metal powder, the presence of the particle can be measured.

Figure 15:
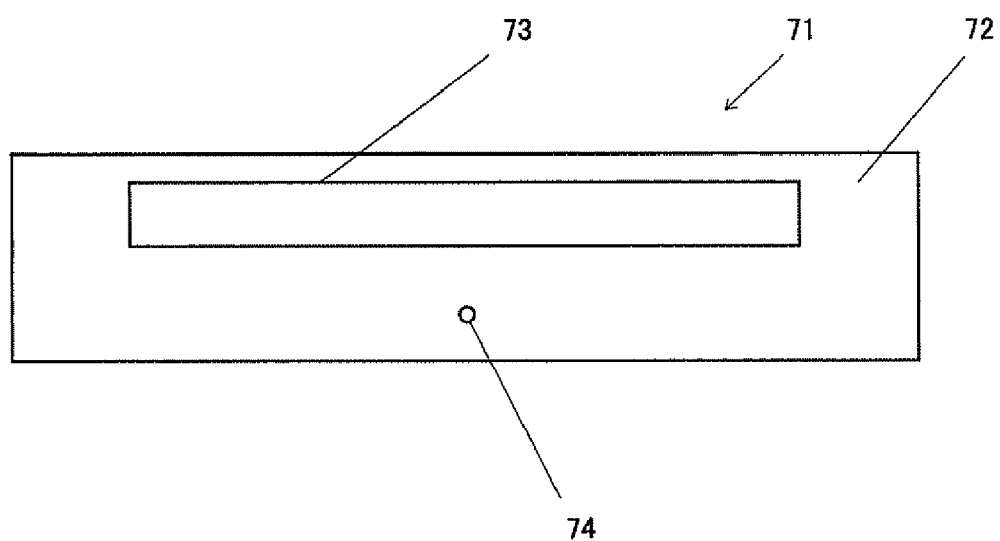
FIG. 15 is a diagram showing the specimen to be provided for the inspection by the nondestructive inspection apparatus using the SQUID magnetic sensor, illustrating another embodiment of the present invention.

FIG. 15 is a diagram showing the specimen to be provided for the inspection by the nondestructive inspection apparatus using the SQUID magnetic sensor, illustrating another embodiment of the present invention.

In this figure, in a magnetized specimen 71, for example, a strip-shaped magnetized member 73 is placed in a rectangular non-magnetized member 72 formed of ceramic, or an insulating member, and a magnetized particle (foreign material) 74 is present on the strip-shaped magnetized member 73 or instead in the non-magnetized member 72.

In this manner, even in the case where the magnetized particle 74 is present in the non-magnetized member 72, the presence of the magnetized particle (foreign material) 74 can be detected accurately, as in the case of FIG. 4.

Next, the arrangement of the belt conveyers for conveying the specimen will be described.

Figure 16:
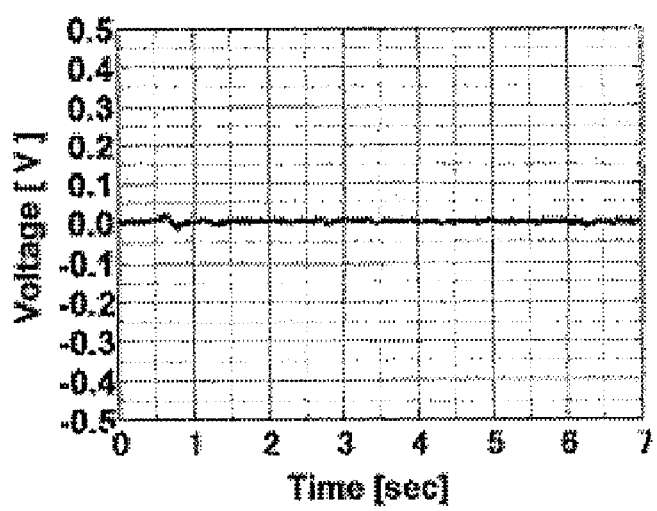
FIG. 16 is a diagram showing comparison of inspection signals obtained using a two-stage conveyer and a one-stage conveyer of the present invention.
Figure 16:
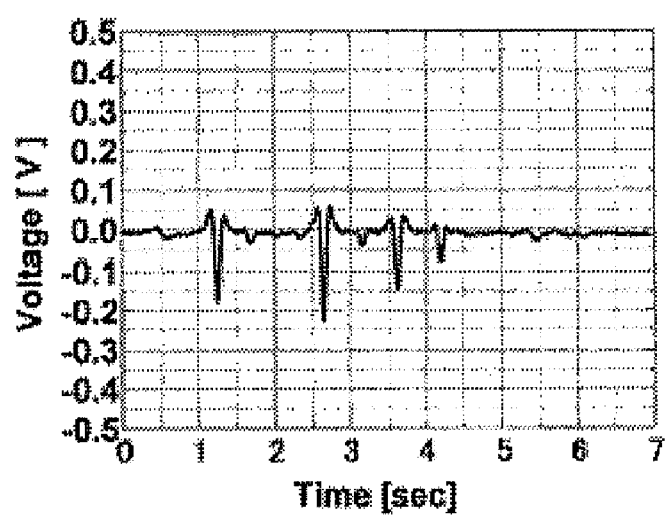

FIG. 16 is a diagram showing comparison of inspection signals obtained using a two-stage conveyer and a one-stage conveyer of the present invention (comparison of the signals at the point after 200 hours has elapsed since the beginning of using the belts), wherein FIG. 16(a) is a diagram showing the case of the two-stage conveyer and FIG. 16(b) is a diagram showing the case of the one-stage conveyer.

The inspection condition here was magnetization direction: horizontal magnetization, approximately 0.1 T, sensor-belt surface distance: 5.5 mm, conveyer velocity: 2.7 m/min., and conversion factor for magnetic flux: 3.4 nT/V.

Instead of the one-stage conveyer in which a single conveyer is used to perform both the polarization of the specimen and the inspection by the SQUID magnetic sensor (gradiometer), the present invention is configured to employ a so-called two-stage conveyer having the first belt conveyer 2 (see FIG. 1) serving as a stage for applying the magnetic field to the specimen and the second belt conveyer 5 (see FIG. 1) serving as an inspection stage of the specimen.

In the case of the one-stage conveyor, as shown in FIG. 16(b), the magnetic noise was observed at the inspection stage at the point after 200 hours had elapsed since the beginning of using the belt. That is, the noise due to the foreign material adhering to the conveyer was approximately 0.2 V, which was a background noise. On the other hand, in the case of the two-stage conveyor, as shown in FIG. 16(a), the magnetic noise was hardly observed even at the same point after 200 hours had elapsed since the beginning of using the belt.

That is, the noise due to the foreign material adhering to the conveyer was approximately 0.02 V, so that the background noise was low and the inspection could be favorably conducted. In comparison, the two-stage conveyer has an advantage in that it can reduce the amplitude of the background noise to approximately 1/10 time of that of the one-stage conveyer.

In detail, metal powder present in the environment or on a rotating unit such as a conveyer roller adheres to the belt conveyer, and is magnetized when the belt conveyer passes under the magnet for magnetization, which generates the magnetic noise.

The magnetized metal powder in such a case is particulate of tens of micrometers or less in diameter, for example, so that it cannot be easily removed by ordinary cleaning or washing once it adheres to the conveyer belt or the like.

Thus, the particulate cannot be easily removed, so that disposing the first belt conveyer 2, which serves as the stage on which the magnetic field is applied to the specimen, and the second belt conveyer 5 separately enables accurate inspection since the second belt conveyer 5 is not involved in the polarization and thus the foreign material that is possibly present on the second belt conveyer 5 is not magnetized.

In this manner, by configuring the measurement apparatus using the two-stage conveyer, the magnetic noise is reduced and the more accurate inspection of the presence and position of the particle can be conducted.

In addition, while the two-stage conveyer described above is effective in the present invention, it is desirable, when employing the one-stage conveyer, to dispose the magnet for horizontal magnetization and the gradiometer in the clean booth or to provide the cleaning means particularly in order to prevent adhesion of contaminants to the specimen and polarization thereof and reduce the magnetic noise generated due to the contaminants at the inspection of the specimen.

Figure 17:
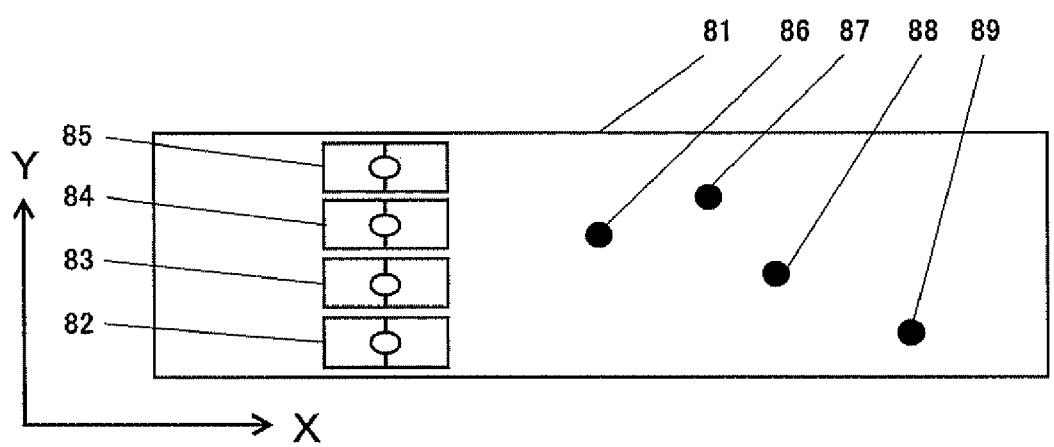
FIG. 17 is a diagrammatic view of the nondestructive inspection apparatus using a plurality of SQUID magnetic sensors (gradiometers), illustrating another embodiment of the present invention.

FIG. 17 is a diagrammatic view of the nondestructive inspection apparatus using a plurality of SQUID magnetic sensors (gradiometers), illustrating another embodiment of the present invention.

In this embodiment, the inspection of magnetized particles 86-89 adhering to a polarized specimen 81 set in the apparatus can be conducted simultaneously in the lateral direction by disposing a plurality of SQUID magnetic sensors (gradiometers) 82-85 in the direction perpendicular to the moving direction of the polarized specimen 81 set in the apparatus.

As described above, the magnetizable member also includes a metal, semiconductor, or insulator having the magnetic material or magnetizable member applied thereto or incorporated therein. In addition, the shape of the magnetizable member is not limited to an elongated body (rectangular body), it may be a square, circular, or ellipsoidal shape.

The present invention should not be limited to the embodiments described above, and a number of variations are possible on the basis of the spirit of the present invention. These variations should not be excluded from the scope of the present invention.

INDUSTRIAL APPLICABILITY

The nondestructive inspection apparatus using the SQUID magnetic sensor of the present invention can be utilized as the inspection apparatus which allows nondestructive and accurate detection of the magnetized particles adhering to or contained in the specimen, and their positional information.

What is claimed is:

1. A nondestructive inspection apparatus using a SQUID magnetic sensor comprising:
   a magnet for horizontal magnetization, the magnet applying a magnetic field to a specimen in the longitudinal direction of the specimen;
   an inspection unit on which the specimen is set, the specimen being horizontally magnetized in the longitudinal direction by the magnet for horizontal magnetization;
   a belt conveyer for conveying the horizontally magnetized specimen; and
   a gradiometer for detecting a particle horizontally magnetized along with a magnetizable member as the horizontally magnetized specimen,
   wherein the belt conveyer includes a first belt conveyer serving as a magnetizing stage on which the magnetic field is applied to the specimen, and a second belt conveyer disposed separately from the first belt conveyer and serving as an inspection stage on which the specimen is inspected.

2. The nondestructive inspection apparatus using the SQUID magnetic sensor according to claim 1, further comprising a cleaning means for removing a foreign material adhering to the belt conveyer after applying the magnetic field.

3. The nondestructive inspection apparatus using the SQUID magnetic sensor according to claim 1, wherein the magnetizable member is disposed in a non-magnetized member.

4. The nondestructive inspection apparatus using the SQUID magnetic sensor according to claim 3, wherein the non-magnetized member is an insulating member.

5. The nondestructive inspection apparatus using the SQUID magnetic sensor according to claim 4, wherein the insulating member is ceramics.

6. The nondestructive inspection apparatus using the SQUID magnetic sensor according to claim 3, wherein the particle is placed in the non-magnetized member.

7. The nondestructive inspection apparatus using the SQUID magnetic sensor according to claim 1, wherein the magnetizable member is a conductive foil having an active material applied thereto.

8. The nondestructive inspection apparatus using the SQUID magnetic sensor according to claim 7, wherein the conductive foil is a copper foil or an aluminum foil.

9. The nondestructive inspection apparatus using the SQUID magnetic sensor according to claim 1, wherein the particle is placed on or in the magnetizable member.

10. The nondestructive inspection apparatus using the SQUID magnetic sensor according to claim 1, wherein the particle is a magnetic material.

11. The nondestructive inspection apparatus using the SQUID magnetic sensor according to claim 10, wherein the magnetic material is iron, nickel, cobalt, or an alloy containing any of iron, nickel, and cobalt.

12. The nondestructive inspection apparatus using the SQUID magnetic sensor according to claim 1, wherein the magnet for horizontal magnetization is a permanent magnet.

13. The nondestructive inspection apparatus using the SQUID magnetic sensor according to claim 1, wherein one-dimensional scanning is conducted by moving the horizontally magnetized specimen in the X direction while the gradiometer remains stationary.

14. The nondestructive inspection apparatus using the SQUID magnetic sensor according to claim 1, wherein the specimen is also inspected in the lateral direction simultaneously by disposing a plurality of gradiometers in the direction perpendicular to the moving direction of the specimen.

* * * * *